US010869966B2

(12) United States Patent
Cupicha et al.

(10) Patent No.: US 10,869,966 B2
(45) Date of Patent: Dec. 22, 2020

(54) SYRINGE SYSTEMS, PISTON SEAL SYSTEMS, STOPPER SYSTEMS, AND METHODS OF USE AND ASSEMBLY

(71) Applicant: Regeneron Pharmaceuticals, Inc., Tarrytown, NY (US)

(72) Inventors: Michael Cupicha, East Schodack, NY (US); Alexei Goraltchouk, Cambridge, MA (US); Ian Hart, Nassau, NY (US); Mike Stelmah, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 101 days.

(21) Appl. No.: 15/048,366

(22) Filed: Feb. 19, 2016

(65) Prior Publication Data

US 2016/0243309 A1 Aug. 25, 2016

Related U.S. Application Data

(60) Provisional application No. 62/118,924, filed on Feb. 20, 2015.

(51) Int. Cl.
*A61M 5/315* (2006.01)
*A61M 5/145* (2006.01)
(Continued)

(52) U.S. Cl.
CPC ...... *A61M 5/31511* (2013.01); *A61M 5/1452* (2013.01); *A61M 5/3129* (2013.01);
(Continued)

(58) Field of Classification Search
CPC .......... A51M 5/31511; A51M 5/31513; A51M 5/315151; A51M 5/3129; A51M 5/1452;
(Continued)

(56) References Cited

U.S. PATENT DOCUMENTS 2,680,439 A 6/1954 Sutermeister
3,028,862 A 4/1962 Prater, Jr.
(Continued)

FOREIGN PATENT DOCUMENTS

CN 1429125 A 7/2003
CN 2675156 Y 2/2005
(Continued)

OTHER PUBLICATIONS

Extended European Search Report dated Nov. 13, 2018, in European Application No. 16753118.5 (10 pages).
(Continued)

*Primary Examiner* — Kevin C Sirmons
*Assistant Examiner* — Tezita Z Watts
(74) *Attorney, Agent, or Firm* — Bookoff McAndrews, PLLC

(57) ABSTRACT

A syringe system, piston seal systems, stopper systems, and methods for assembling and using the syringe systems. The piston seal system including a piston seal member and a piston head member. The injection system including a container, a piston seal system positioned within the container, and a stopper system coupled to an end of the container. The method of assembling an injection system, the method includes obtaining a container, a piston seal system, and a stopper system. The method also includes inserting the piston seal system into a cavity within the container. The method further includes securing the stopper system at an end of the container in an opening of the cavity. Methods of using the syringe system, piston seal systems, and stopper systems are also disclosed.

21 Claims, 19 Drawing Sheets

(51) Int. Cl.
*A61M 5/31* (2006.01)
*F16J 1/00* (2006.01)
*F16J 9/20* (2006.01)

(52) U.S. Cl.
CPC .... *A61M 5/31513* (2013.01); *A61M 5/31515* (2013.01); *F16J 1/005* (2013.01); *F16J 9/20* (2013.01); *A61M 5/14526* (2013.01); *A61M 2005/3131* (2013.01); *A61M 2005/31523* (2013.01); *A61M 2207/00* (2013.01)

(58) Field of Classification Search
CPC ...... A51M 5/14526; A61M 2005/3131; A61M 2005/31523; F16J 9/20; F16J 1/005
See application file for complete search history.

(56) References Cited

U.S. PATENT DOCUMENTS

| | | | |
|---|---|---|---|
| 3,075,525 A | 1/1963 | McConnaughey | |
| 3,460,534 A | 8/1969 | Black | |
| 4,231,494 A | 11/1980 | Greenwood | |
| 4,424,057 A * | 1/1984 | House | A61M 5/31596 604/88 |
| 4,437,859 A | 3/1984 | Whitehouse et al. | |
| 4,505,701 A | 3/1985 | Navato | |
| 4,861,340 A | 8/1989 | Smith et al. | |
| 5,425,715 A | 6/1995 | Dalling et al. | |
| 5,586,975 A * | 12/1996 | Tanaka | A61M 5/31513 604/191 |
| 5,616,132 A | 4/1997 | Newman | |
| 5,865,803 A | 2/1999 | Major | |
| 6,045,534 A | 4/2000 | Jacobsen et al. | |
| 6,186,982 B1 | 2/2001 | Gross et al. | |
| 6,193,695 B1 | 2/2001 | Rippstein, Jr. | |
| 6,500,150 B1 | 12/2002 | Gross et al. | |
| 6,511,459 B1 | 1/2003 | Fago | |
| 6,595,956 B1 | 7/2003 | Gross et al. | |
| 6,673,035 B1 | 1/2004 | Rice et al. | |
| 6,682,504 B2 | 1/2004 | Nelson et al. | |
| 6,824,529 B2 | 11/2004 | Gross et al. | |
| 6,843,782 B2 | 1/2005 | Gross et al. | |
| 6,960,184 B2 | 11/2005 | Willis et al. | |
| 7,104,971 B2 | 9/2006 | Hjertman | |
| 7,416,540 B2 | 8/2008 | Edwards et al. | |
| 7,449,012 B2 | 11/2008 | Young et al. | |
| 7,648,482 B2 | 1/2010 | Edwards et al. | |
| 7,648,483 B2 | 1/2010 | Edwards et al. | |
| 7,654,983 B2 | 2/2010 | De La Serna et al. | |
| 7,731,686 B2 | 6/2010 | Edwards et al. | |
| 7,731,690 B2 | 6/2010 | Edwards et al. | |
| 7,740,607 B2 | 6/2010 | Willis et al. | |
| 7,744,563 B2 | 6/2010 | Landau et al. | |
| 7,749,194 B2 | 7/2010 | Edwards et al. | |
| 7,824,373 B2 | 11/2010 | Kim et al. | |
| 7,857,167 B1 | 12/2010 | Hollars | |
| 7,918,823 B2 | 4/2011 | Edwards et al. | |
| 7,947,017 B2 | 5/2011 | Edwards et al. | |
| 8,016,788 B2 | 9/2011 | Edwards et al. | |
| 8,021,344 B2 | 9/2011 | Edwards et al. | |
| 8,105,281 B2 | 1/2012 | Edwards et al. | |
| 8,118,777 B2 | 2/2012 | Ducharme et al. | |
| 8,123,719 B2 | 2/2012 | Edwards et al. | |
| 8,172,797 B2 | 5/2012 | Hoegdahl | |
| 8,206,360 B2 | 6/2012 | Edwards et al. | |
| 8,226,610 B2 | 7/2012 | Edwards et al. | |
| 8,231,573 B2 | 7/2012 | Edwards et al. | |
| 8,303,535 B2 | 11/2012 | Both et al. | |
| 8,308,697 B2 | 11/2012 | Stamp et al. | |
| 8,313,463 B2 | 11/2012 | Barrow-Williams et al. | |
| 8,313,466 B2 | 11/2012 | Edwards et al. | |
| 8,343,110 B2 | 1/2013 | Harrison et al. | |
| 8,361,026 B2 | 1/2013 | Edwards et al. | |
| 8,361,029 B2 | 1/2013 | Edwards et al. | |
| 8,361,054 B2 | 1/2013 | Ducharme et al. | |
| 8,425,462 B2 | 4/2013 | Edwards et al. | |
| 8,480,624 B2 | 7/2013 | Kim et al. | |
| 8,608,698 B2 | 12/2013 | Edwards et al. | |
| 8,622,973 B2 | 1/2014 | Edwards et al. | |
| 8,627,816 B2 | 1/2014 | Edwards et al. | |
| 8,636,704 B2 | 1/2014 | Shang et al. | |
| 8,668,670 B2 | 3/2014 | Bicknell et al. | |
| 8,679,061 B2 | 3/2014 | Julian et al. | |
| 8,690,827 B2 | 4/2014 | Edwards et al. | |
| 8,708,958 B2 | 4/2014 | Kim et al. | |
| 8,708,968 B2 | 4/2014 | Julian et al. | |
| 8,728,032 B2 | 5/2014 | Ducharme et al. | |
| 8,758,301 B2 | 6/2014 | Shang et al. | |
| 8,899,987 B2 | 12/2014 | Edwards et al. | |
| 8,920,367 B2 | 12/2014 | Edwards et al. | |
| 8,920,377 B2 | 12/2014 | Edwards et al. | |
| 8,926,594 B2 | 1/2015 | Edwards et al. | |
| 8,932,252 B2 | 1/2015 | Edwards et al. | |
| 8,939,943 B2 | 1/2015 | Edwards et al. | |
| 8,992,476 B2 | 3/2015 | Shang et al. | |
| 9,017,287 B2 | 4/2015 | Bicknell et al. | |
| 9,022,022 B2 | 5/2015 | Edwards et al. | |
| 9,022,980 B2 | 5/2015 | Edwards et al. | |
| 9,056,170 B2 | 6/2015 | Edwards et al. | |
| 9,084,849 B2 | 7/2015 | Edwards et al. | |
| 9,101,744 B2 | 8/2015 | Ducharme | |
| 9,119,920 B2 | 9/2015 | Cowe | |
| 9,149,579 B2 | 10/2015 | Edwards et al. | |
| D744,005 S | 11/2015 | Anderson et al. | |
| 9,173,999 B2 | 11/2015 | Edwards et al. | |
| 9,180,244 B2 | 11/2015 | Anderson et al. | |
| 9,238,108 B2 | 1/2016 | Edwards et al. | |
| 9,259,539 B2 | 2/2016 | Edwards et al. | |
| 9,265,887 B2 | 2/2016 | Julian et al. | |
| 9,278,177 B2 | 3/2016 | Edwards et al. | |
| 9,278,182 B2 | 3/2016 | Edwards et al. | |
| 9,327,077 B2 | 5/2016 | Edwards et al. | |
| 9,339,610 B2 | 5/2016 | Julian et al. | |
| 9,352,091 B2 | 5/2016 | Edwards et al. | |
| 9,375,533 B2 | 6/2016 | Ducharme et al. | |
| 9,408,973 B2 | 8/2016 | Shang et al. | |
| 9,443,445 B2 | 9/2016 | Laurusonis et al. | |
| 9,474,869 B2 | 10/2016 | Edwards et al. | |
| 9,486,584 B2 | 11/2016 | Julian et al. | |
| 9,498,574 B2 | 11/2016 | Davis et al. | |
| 9,517,307 B2 | 12/2016 | Blondino et al. | |
| 9,522,235 B2 | 12/2016 | Edwards et al. | |
| 9,542,826 B2 | 1/2017 | Edwards et al. | |
| 9,550,025 B2 | 1/2017 | Dunn et al. | |
| 9,555,191 B2 | 1/2017 | Edwards et al. | |
| 9,561,328 B2 | 2/2017 | Shang et al. | |
| 9,572,938 B2 | 2/2017 | Julian et al. | |
| 9,623,183 B2 | 4/2017 | Jennings et al. | |
| 9,636,460 B1 | 5/2017 | Jaeger et al. | |
| 9,675,754 B2 | 6/2017 | Desalvo et al. | |
| 9,724,471 B2 | 8/2017 | Edwards et al. | |
| 9,731,080 B2 | 8/2017 | Douglas Ivan et al. | |
| 9,737,669 B2 | 8/2017 | Edwards et al. | |
| 9,764,090 B2 | 9/2017 | Bicknell et al. | |
| 9,805,620 B2 | 10/2017 | Edwards et al. | |
| 9,814,838 B2 | 11/2017 | Edwards et al. | |
| 9,821,117 B2 | 11/2017 | Anderson et al. | |
| 9,833,573 B2 | 12/2017 | Edwards et al. | |
| 9,836,948 B2 | 12/2017 | Edwards et al. | |
| 9,867,931 B2 | 1/2018 | Gittard et al. | |
| 9,867,938 B2 | 1/2018 | Edwards et al. | |
| 9,878,102 B2 | 1/2018 | Julian et al. | |
| 9,911,308 B2 | 3/2018 | Edwards et al. | |
| 10,039,879 B2 | 8/2018 | Davis et al. | |
| 2001/0021828 A1 * | 9/2001 | Fischer | A61M 5/31511 604/218 |
| 2004/0073169 A1 | 4/2004 | Amisar et al. | |
| 2005/0043689 A1 | 2/2005 | Chen | |
| 2005/0209562 A1 | 9/2005 | Kim | |
| 2007/0185437 A1 | 8/2007 | Goldenberg et al. | |
| 2009/0082737 A1 | 3/2009 | Bobst et al. | |
| 2009/0118680 A1 | 5/2009 | Goldbrunner et al. | |
| 2011/0060291 A1 | 3/2011 | Beccaro et al. | |
| 2011/0091331 A1 | 4/2011 | Moutafis et al. | |

(56) References Cited

U.S. PATENT DOCUMENTS

| | | | |
|---|---|---|---|
| 2012/0191102 A1* | 7/2012 | Matsumoto | A61M 5/14526 606/94 |
| 2013/0274677 A1 | 10/2013 | Ekman et al. | |
| 2014/0114248 A1 | 4/2014 | Desalvo et al. | |
| 2014/0114250 A1 | 4/2014 | DeSalvo et al. | |
| 2014/0128840 A1 | 5/2014 | Rao et al. | |
| 2014/0148784 A1 | 5/2014 | Anderson et al. | |
| 2014/0207073 A1 | 7/2014 | Shang et al. | |
| 2014/0276411 A1 | 9/2014 | Cowan et al. | |
| 2014/0276415 A1* | 9/2014 | Davis | A61M 5/14526 604/150 |
| 2014/0276451 A1 | 9/2014 | Cowan et al. | |
| 2014/0276614 A1* | 9/2014 | Flores | A61M 5/1456 604/510 |
| 2014/0296824 A1 | 10/2014 | Edwards et al. | |
| 2014/0358117 A1 | 12/2014 | Shang et al. | |
| 2015/0037772 A1 | 2/2015 | Julian et al. | |
| 2015/0314073 A1 | 11/2015 | Shang et al. | |
| 2016/0022909 A1 | 1/2016 | Edwards et al. | |
| 2016/0045670 A1 | 2/2016 | Edwards et al. | |
| 2016/0121056 A1 | 5/2016 | Edwards et al. | |
| 2016/0184521 A1 | 6/2016 | Edwards et al. | |
| 2016/0184535 A1 | 6/2016 | Edwards et al. | |
| 2016/0199579 A1 | 7/2016 | Boyd et al. | |
| 2016/0235916 A1 | 8/2016 | Edwards et al. | |
| 2016/0279323 A1 | 9/2016 | Willoughby et al. | |
| 2016/0303327 A1 | 10/2016 | Moren | |
| 2016/0361496 A1 | 12/2016 | Guillermo et al. | |
| 2017/0035957 A1 | 2/2017 | Edwards et al. | |
| 2017/0049954 A1 | 2/2017 | Edwards et al. | |
| 2017/0072134 A1 | 3/2017 | Fish et al. | |
| 2017/0143904 A1 | 5/2017 | Dunne | |
| 2017/0182242 A1 | 6/2017 | Galitz et al. | |
| 2017/0203041 A1 | 7/2017 | Julian et al. | |
| 2017/0232206 A1 | 8/2017 | Blondino et al. | |
| 2017/0246392 A1 | 8/2017 | Desalvo et al. | |
| 2017/0290982 A1 | 10/2017 | Edwards et al. | |
| 2017/0304548 A1 | 10/2017 | Chen et al. | |
| 2017/0312433 A1 | 11/2017 | Edwards et al. | |
| 2017/0312457 A1 | 11/2017 | Desalvo et al. | |
| 2017/0348488 A1 | 12/2017 | Bechmann et al. | |
| 2018/0008774 A1 | 1/2018 | Edwards et al. | |
| 2018/0008775 A1 | 1/2018 | Stefanov | |

FOREIGN PATENT DOCUMENTS

| | | |
|---|---|---|
| DE | 10015616 A1 | 10/2001 |
| EP | 2058020 A2 | 5/2009 |
| EP | 2401012 A1 | 1/2012 |
| EP | 2221076 B1 | 4/2013 |
| EP | 2686036 A1 | 1/2014 |
| EP | 1441787 B2 | 2/2014 |
| EP | 2820640 A1 | 1/2015 |
| EP | 3020428 A1 | 5/2016 |
| EP | 2699286 B1 | 8/2016 |
| EP | 3089772 A2 | 11/2016 |
| EP | 3089773 A1 | 11/2016 |
| EP | 3089774 A1 | 11/2016 |
| JP | 61-164564 A | 7/1986 |
| JP | H07299141 A | 11/1995 |
| JP | 2001-321437 A | 11/2001 |
| JP | 2013-63276 A | 4/2013 |
| WO | 2004067067 A1 | 8/2004 |
| WO | 2006083876 A2 | 8/2006 |
| WO | 2007131367 A1 | 11/2007 |
| WO | 2008064092 A2 | 5/2008 |
| WO | 2008091838 A2 | 7/2008 |
| WO | 2008103997 A2 | 8/2008 |
| WO | 2010138703 A1 | 12/2010 |
| WO | 2011023629 A1 | 3/2011 |
| WO | 2011133823 A1 | 10/2011 |
| WO | 2012045836 A2 | 4/2012 |
| WO | 2012145752 A2 | 10/2012 |
| WO | 2012145752 A8 | 2/2013 |
| WO | 2013182858 | 12/2013 |
| WO | 2014/059444 A2 | 4/2014 |
| WO | 2014066461 A1 | 5/2014 |
| WO | 2015172686 A1 | 11/2015 |
| WO | 2016154427 A2 | 9/2016 |
| WO | 2016205403 A2 | 12/2016 |
| WO | 2017181297 A1 | 10/2017 |
| WO | 2018013493 A1 | 1/2018 |

OTHER PUBLICATIONS

Chinese Office Action dated Nov. 5, 2019, in Chinese Application No. 201680022806.8 (8 pages).

Examination report No. 1 for standard patent application dated Dec. 16, 2019 in Australian Application No. 2016219904 (6 pages).

"Epinephrine Auto Injector | Auvi-Q (epinephrine injection, USP)," https://web.archive.org/web/20140122125239/https://www.auvi-q.com/, Jan. 22, 2014, 1 page.

"Nuance Designs | next generation drug delivery technology," https://web.archive.org/web/20140517123659/http://nuance-designs.com/, May 17, 2014, 2 pages.

"The Medical House Receives FDA Approval for Autoinjector," Pharmaceutical Online, https://www.pharmaceuticalonline.com/doc/the-medical-house-receives-fda-approval-for-a-0001, Mar. 14, 2008, 3 pages.

"Syrina | Injectables Devices & Technology | Bespak," https://web.archive.org/web/20160316221015/https://bespak.com/devices-technologies/injectables/syrina/, Mar. 16, 2016, 8 pages.

Japanese Office Action dated Jan. 14, 2020, in Japanese Application No. 2017-544004 (6 pages).

International Search Report and Written Opinion issued in PCT/US2016/018609, dated Jun. 23, 2016.

Japanese Office Action dated Jul. 28, 2020, in Japanese Application No. 2017-544004 (5 pages).

* cited by examiner

SYRINGE SYSTEMS, PISTON SEAL SYSTEMS, STOPPER SYSTEMS, AND METHODS OF USE AND ASSEMBLY

CROSS REFERENCE TO RELATED APPLICATION

This application claims priority benefit under 35 U.S.C. § 119(e) to U.S. provisional application No. 62/118,924 filed Feb. 20, 2015, which is incorporated herein by reference in its entirety.

FIELD OF THE INVENTION

The present invention relates generally to drug delivery systems for administering medication. More specifically, but not exclusively, the present invention concerns syringe systems, piston seal systems, and stopper systems.

BACKGROUND OF THE INVENTION

Currently many injectors and assisted injection systems use a plunger rod to actuate the piston head and deliver the medication to the patient. The plunger rod may not provide uniform, consistent, or controlled injections to a patient. In addition, the currently used piston head and plunger rod systems may allow for the driving fluid of an assisted injection system to leak past the piston head and contaminate the medication. Thus, injectors and assisted injection systems that provide more uniform, consistent and controlled injections and prevent contamination of the medication being administered are needed.

SUMMARY OF THE INVENTION

Aspects of the present invention provide a syringe system, piston seal systems, and stopper systems. The present invention also provides methods for assembling and using the syringe systems.

In one aspect provided herein is a piston seal system including a piston seal member and a piston head member.

In another aspect, provided herein is an injection system including a container, a piston seal system positioned within the container, and a stopper system coupled to an end of the container.

In yet another aspect, provided herein is a method of assembling an injection system, the method includes obtaining a container, a piston seal system, and a stopper system. The method also includes inserting the piston seal system into a cavity within the container. The method further includes securing the stopper system at an end of the container in an opening of the cavity.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein are syringe systems, piston seal systems, and stopper systems. Further, methods of assembling and using the syringe systems, piston seal systems, and stopper systems are discussed.

In this detailed description and the following claims, the words proximal, distal, anterior, posterior, medial, lateral, superior and inferior are defined by their standard usage for indicating a particular part of a device according to the relative disposition of the device with respect to a body or directional terms of reference. For example, "proximal" means the portion of a device nearest the point of injection, while "distal" indicates the portion of the device farthest from the point of injection. As for directional terms, "anterior" is a direction towards the front side of the device, "posterior" means a direction towards the back side of the device, "medial" means towards the midline of the device, "lateral" is a direction towards the sides or away from the midline of the device, "superior" means a direction above and "inferior" means a direction below another object or structure.

Figure 2:
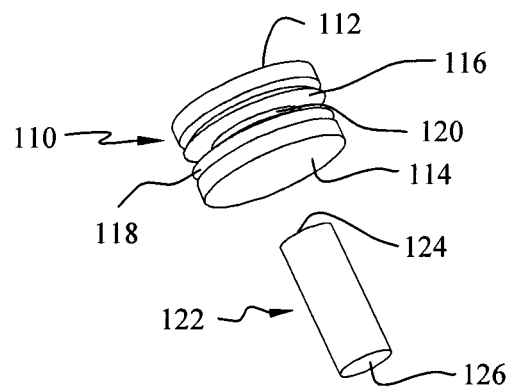
FIG. 2 is an exploded bottom perspective view of the piston seal system of FIG. 1, in accordance with an aspect of the present invention.
Figure 2:
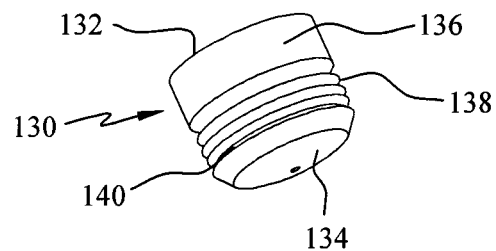
Figure 3:
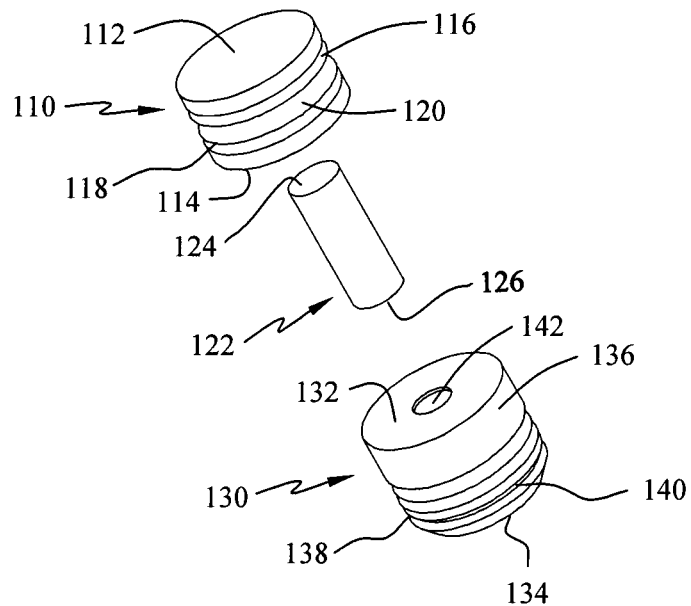
FIG. 3 is an exploded top perspective view of the piston seal system of FIG. 1, in accordance with an aspect of the present invention.
Figure 4:
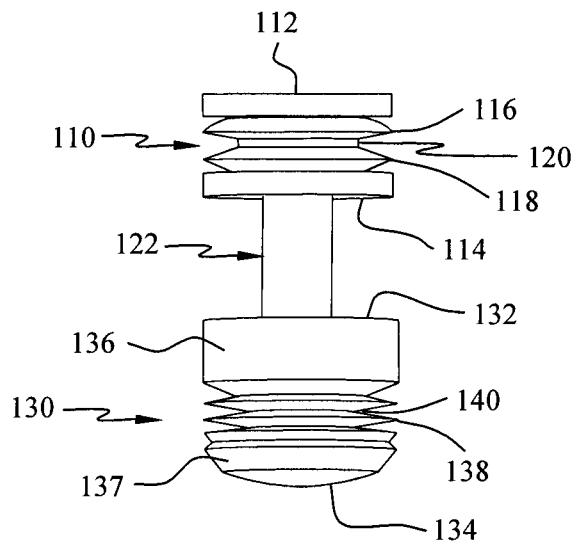
FIG. 4 is a side view of the piston seal system of FIG. 1, in accordance with an aspect of the present invention.
Figure 5:
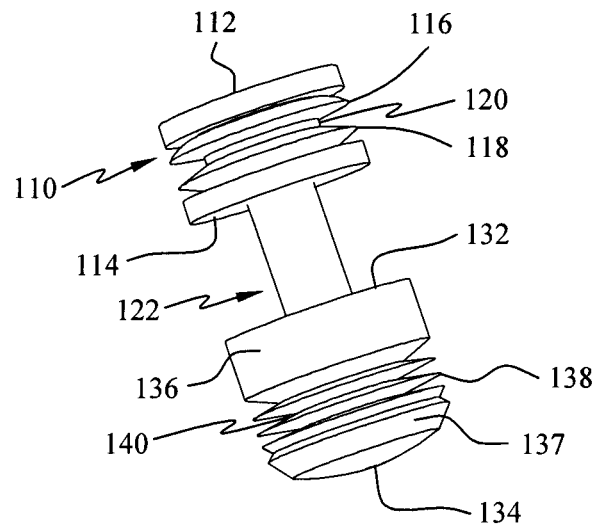
FIG. 5 is a perspective view of the piston seal system of FIG. 1, in accordance with an aspect of the present invention.

Referring to the drawings, wherein like reference numerals are used to indicate like or analogous components throughout the several views, and with particular reference to FIGS. 1-5, there is illustrated a syringe piston seal system 100. The piston seal system 100 may include a piston seal member 110, a coupling member 122, and a piston head member 130. The coupling member 122 may include a first end 124 and a second end 126. The first end 124 of the coupling member 122 may be secured to a second end 114 of the piston seal member 110, as shown in FIGS. 4 and 5. While the second end 126 of the coupling member 122 may be secured to the first end 132 of the piston head member 130, as shown in FIGS. 4 and 5. The coupling member 122 may have, for example, a diameter that is smaller than the diameter of the seal member 110 and the head member 130. The coupling member 122 acts to create a pressure relief space between the second end 114 of the seal member 110 and the first end 132 of the head member 130, as shown in FIGS. 4 and 5. The coupling member 122 may also act to create a space between the seal member 110 and head member 130 to trap any leaked fluid and prevent contamination of the medication being delivered.

Figure 29:
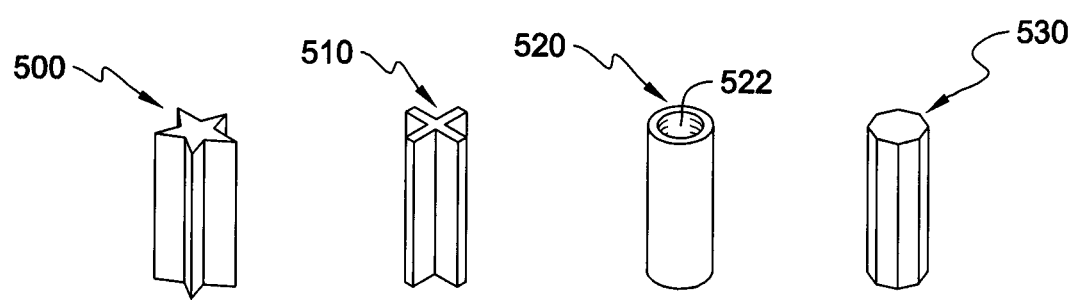
FIG. 29 is a side perspective view of a several alternative embodiments of a coupling member of the piston seal system of FIG. 1, in accordance with an aspect of the present invention.

Although only a cylindrical coupling member 122 with a circular cross section is illustrated, it is also contemplated that the coupling member 122 may have, for example, a cross section with a polygonal, star, truss, donut, or any other shape. For example as shown in FIG. 29, a coupling mechanism 500 with a star shape, a coupling mechanism 510 with an "X" shape, a coupling mechanism 520 with an "O" or donut shape including an opening 522 extending from the first end to the second end, and a coupling mechanism 530 with an octagon shape may be used. The shape of the coupling member 122 may be selected to provide support to the seal member 110 to prevent any angular shift or tilting of the seal member 110 when pressure is applied to the first end 112.

Figure 1:
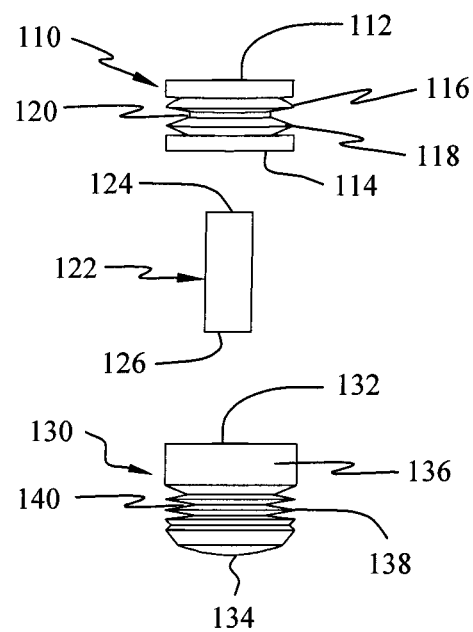
FIG. 1 is an exploded side view of a piston seal system, in accordance with an aspect of the present invention.

The piston seal system 100 may be, for example, a three piece construct as shown in FIGS. 1-3 or alternatively may be a one piece construct as shown in FIGS. 4 and 5. The three piece construct embodiment may have a coupling member 122 with a first end 124 and a second end 126. The first and second ends 124, 126 may be threaded to mate with corresponding threads in an opening in the second end 114 of the piston seal member 110 and the first end 132 of the piston head member 130. Alternatively, it is also contemplated that the coupling member 122 may be attached to the piston seal member 110 and the piston head member 130 by, for example, an adhesive, ultrasonic bonding, thermal melt, press fit, and the like. The one piece construct embodiment of the piston seal system 100 may be a molded or an otherwise formed piston seal system 100 as shown in FIGS. 4 and 5. Other configurations of the pieces of the piston seal system 100 are also contemplated to form the piston seal system 100, as shown in FIGS. 4 and 5, with a piston seal member 110 spaced apart from a piston head member 130.

With continued reference to FIGS. 1-5, the piston seal member 110 may include a first base portion at the first end 112 and a second base portion at the second end 114. The piston seal member 110 may also have, for example, at least one flange member, for example, a first flange member 116 and a second flange member 118. The terms "flange member," "flexible member," "ribs," and "rings" may be used interchangeably herein as they essentially refer to the same structure. The flange members 116, 118 are circumferential and have the same circumference as ends 112, 114 to ensure continuous contact with the walls of the syringe and capture of liquid. The space between the flange members 116, 118 allows for deformity to maximize contact with the syringe wall during movement. It is contemplated that the piston seal member 110 may include a plurality of flange members 116, 118. The number of flange members 116, 118 may range from, for example, the minimum number of flange members 116, 118 necessary to affect a seal and prevent fluid from passing through the piston seal member 110 to the maximum number of flange members 116, 118 which still allow the piston seal member 110 to slide within a container, chamber, syringe, vial, or cartridge. In one embodiment, the piston seal member 110 may include, for example, approximately zero to four flange members 116, 118.

In addition, the piston seal member 110 may have a recess or groove 120 positioned between the flange members 116, 118. The second end 114 of the piston seal member 110 may include an opening (not shown) for receiving the coupling member 122. The first end 112 and second end 114 may each be sized to be received within a syringe container, syringe chamber, or patch pump vial device (not shown). The first and second ends 112, 114 are sized to allow for movement while preventing the pressurized media used to inject the medication from passing by the piston seal member 110 and contaminating the sterile medication at the proximal end of the container, chamber, or vial. In addition, the at least one flange member 116, 118 may also be sized to engage the sidewall of the container, chamber, or vial to assist with preventing the pressurized media from passing by the piston seal member 110 and contaminating the sterile medication, as described in greater detail below. The piston seal member 110 also provides a pressure relief area for the system 100.

The piston head member 130, as shown in FIGS. 1-5, may include, for example, a first base portion 136 at the first end 132 and a second base portion 137 at the second end 134. The first base portion 136 may be, for example, thicker than the second base portion 137. The piston head member 130 may also include at least one flange member 138 and at least one recess or groove 140 positioned between the first base portion 136 at the first end 132 and the second base portion 137 at the second end 134. The first base portion 136 and second base portion 137 may be sized to be received within a syringe container, syringe chamber, or patch pump vial device (not shown) to prevent medication from passing to the distal end of the container, chamber, or vial during injection through a fluid pathway at the proximal end of the container, chamber, syringe, vial, or cartridge. The piston head member 130 by preventing medication from passing to the distal end of the container, chamber, syringe, vial, or cartridge, maintains the sterility of the medication. The at least one flange member 138 may also be sized to engage the sidewall of the container, chamber, or vial and assist with preventing the medication from passing by the piston head member 130 toward the distal end of the container, chamber, or vial to ensure the proper dosage of medication is delivered to the patient. The circumference and space between the at least one flange member 138 and first and second base portions 136, 137 allows for maximum contact between the at least one flange member 138 and the sidewall of the container, chamber, or vial. It is contemplated that the piston head member 130 may include a plurality of flange members 138. The number of flange members 138 may range from, for example, the minimum number of flange members 138 necessary to affect a seal and prevent fluid from passing through the piston head member 130 to the maximum number of flange members 138 which still allow the piston head member 130 to slide within a container, chamber, syringe, vial, or cartridge. In one embodiment, the piston head member 130 may include, for example, approximately two to five flange members 138.

Figure 6:
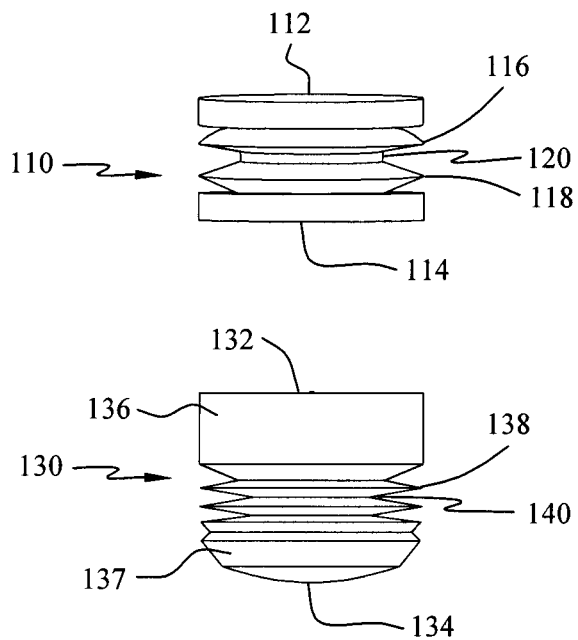
FIG. 6 is a side view of another piston seal system, in accordance with an aspect of the present invention.
Figure 7:
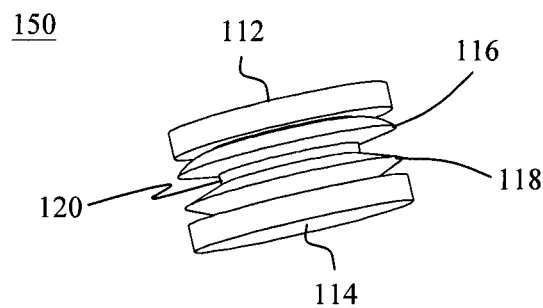
FIG. 7 is a perspective view of the piston seal system of FIG. 6, in accordance with an aspect of the present invention.
Figure 7:
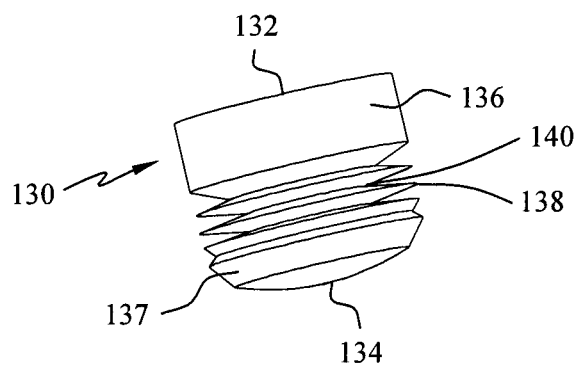

Referring now to FIGS. 6 and 7, another piston seal system 150 is shown. The piston seal system 150 is a two piece system. The piston seal system 150 may include a piston seal member 110 and a piston head member 130. The piston seal member 110 and piston head member 130 may be the same as described above with reference to FIGS. 1-5 and will not be described again here for brevity sake. The seal member 110 and head member 130 may be positioned in a container, chamber, or vial spaced apart to leave a pressure relief space between the seal member 110 and the head member 130. During an injection a force may be applied on the seal member 110 which will in turn apply a force on the head member 130 to translate the head member 130 and deliver the medication to a patient. The force applied to the seal member 110 may cause the second end 114 of the seal member 110 to directly contact the first end 132 of the head member 130 to move the head member 130. The second end 114 of the seal member 110 and the first end 132 of the head member 130 may have, for example, matching sizes and configurations to allow for the second end 114 to completely contact the first end 132.

Figure 8:
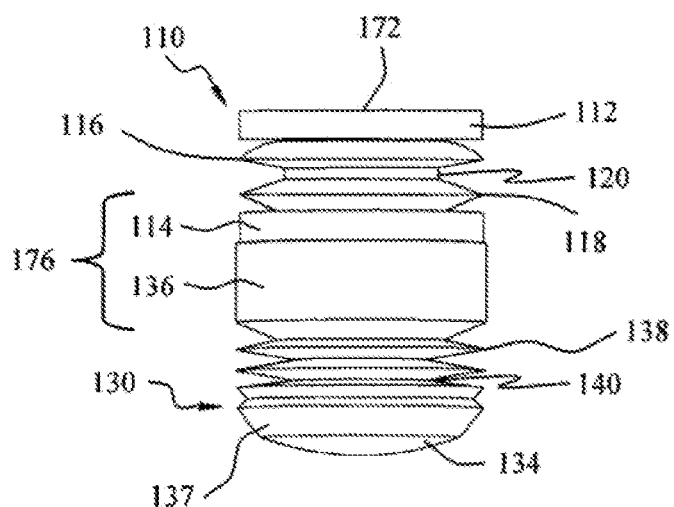
FIG. 8 is a side view of yet another piston seal system, in accordance with an aspect of the present invention.
Figure 9:
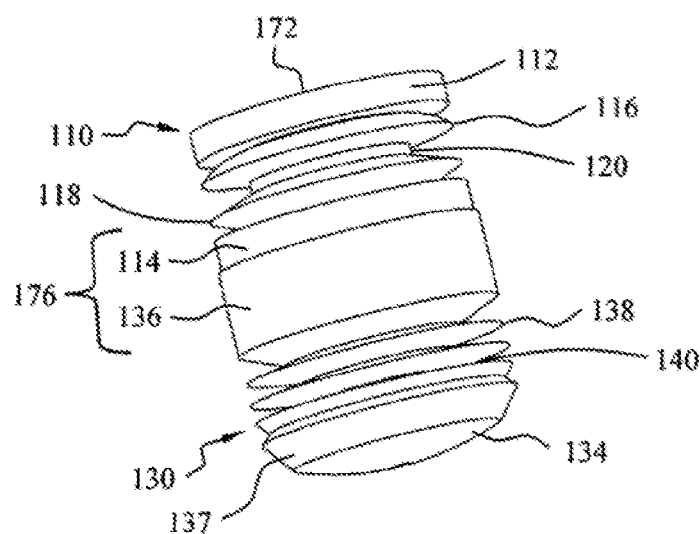
FIG. 9 is a perspective view of the piston seal system of FIG. 8, in accordance with an aspect of the present invention.

Another piston seal system 170 is shown in FIGS. 8 and 9. The piston seal system 170 is a one piece system. The piston seal system 170 may include a piston seal member 110 including flanges 116, 118 directly attached to a piston head member 130 including flanges 138. The seal member 110 and head member 130 may be the same as described above with reference to FIGS. 1-5 and will not be described again here for brevity sake. However, the base portion at the second end 114 of the seal member 110 and the base portion 136 of the head member 130 may be, for example, secured together or alternatively be formed as a single piece creating an intermediate portion 176. The intermediate portion 176 may act as the barrier between the seal member 110 and the head member 130. The piston seal system 170 may be, for example, molded or formed as a unitary piece. The piston seal system 170 may be used in a reusable container, chamber, or vial as it allows for the seal member 110 and head member 130 to move together enabling both injection from and filling of the container, chamber, or vial.

Figure 10:
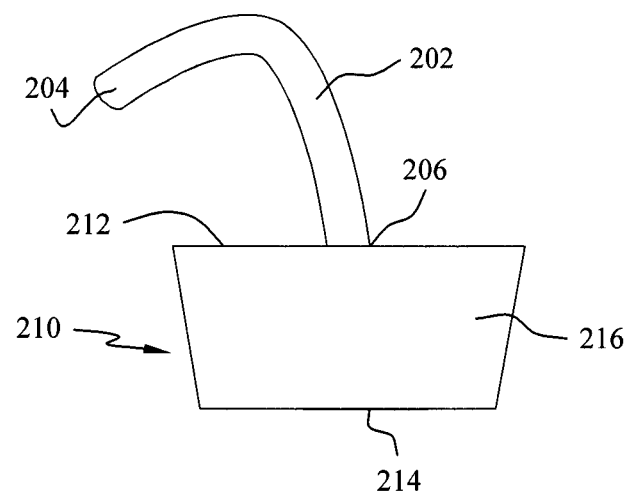
FIG. 10 is a side view of a stopper member and tube, in accordance with an aspect of the present invention.
Figure 11:
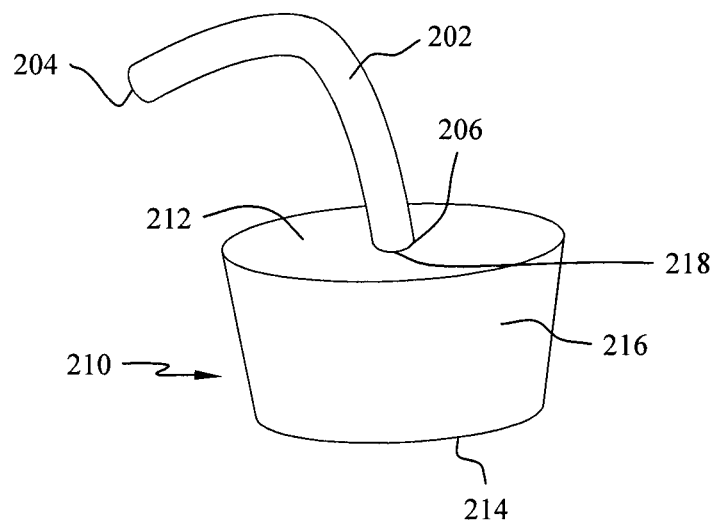
FIG. 11 is a top perspective view of the stopper member and tube of FIG. 10, in accordance with an aspect of the present invention.

FIGS. 10 and 11 show one embodiment of a stopper system 200. The stopper system 200 may include a pressure delivery device 202 and a stopper member 210. The stopper system 200 may be secured into the end of a container, chamber, or vial, as described in greater detail below, to allow for delivery of a pressurized media to the distal end of the container, chamber, or vial. The pressure delivery device 202 may include a first end 204 and a second end 206. The first end 204 may be coupled to a pressure delivery system for injection of a fluid into the container, chamber, or vial to activate delivery of a medication to a patient. The fluid may be, for example, a liquid, gas, air, or the like. The second end 206 may be coupled to the stopper member 210 at a first end 212. The stopper member 210 may include the first end 212 and a second end 214 opposite the first end 212. The stopper member 210 may also include a sidewall 216 extending between the first end 212 and the second end 214. The sidewall 216 may be straight, tapered, arced, or otherwise shaped to be secured within the opening in the container, chamber, or vial. The stopper member 210 may also include an opening 218, as shown in FIG. 11. The opening 218 may extend from the first end 212 to the second end 214 to receive the pressure delivery device 202 and allow for passage of the pressurized fluid.

Figure 12:
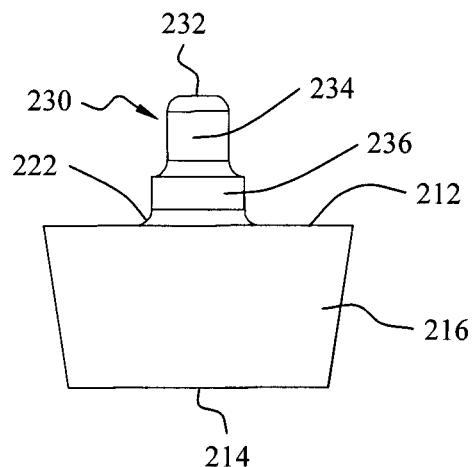
FIG. 12 is a side view of another stopper member, in accordance with an aspect of the present invention.
Figure 13:
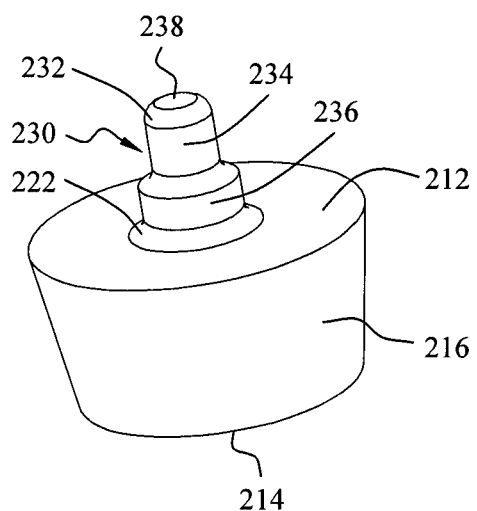
FIG. 13 is a top perspective view of the stopper member of FIG. 12, in accordance with an aspect of the present invention.

Another embodiment of a stopper member 220 is shown in FIGS. 12 and 13. The stopper member 220 may include a first end 212, a second end 214 opposite the first end 212, a sidewall 216 extending between the first end 212 and second end 214, and a fitting member 230. The fitting member 230 may be secured to the first end 212 of the stopper member 220 at a coupling portion 222. The fitting member 230 may include a first end 232, a receiving portion 234, and a base portion 236. The receiving portion 234 may be sized to be secured to a pressure delivery device, such as devices 190, 202, as described in greater detail below with reference to FIGS. 20 and 21. The base portion 236 may be secured to the coupling portion 222 to secure the fitting member 230 to the first end 212. The base portion 236 may have, for example, a larger diameter than the receiving portion 234. The stopper member 220 may also include an opening 238, as shown in FIG. 13, which extends from the first end 232 of the fitting member 230 through to the second end 214 of the stopper member 220. The opening 238 allows for a pressurized media to pass through the stopper member 220 and into the container, chamber, or vial (not shown).

Figure 14:
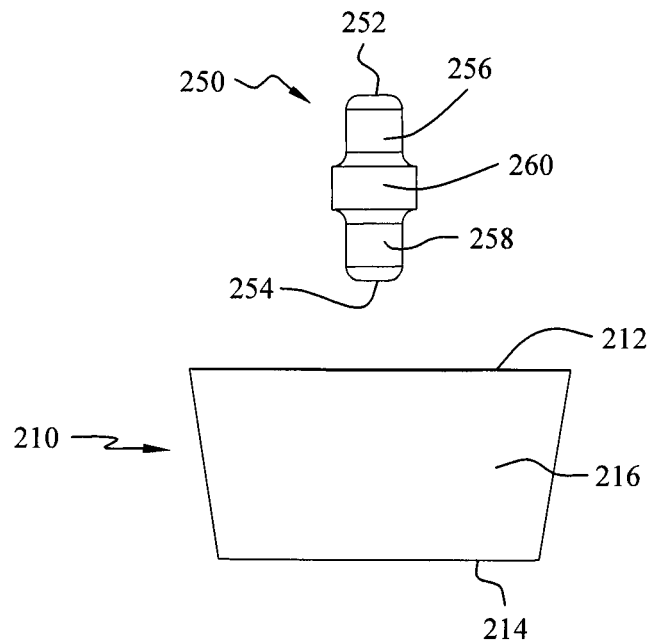
FIG. 14 is a side view of yet another stopper member, in accordance with an aspect of the present invention.
Figure 15:
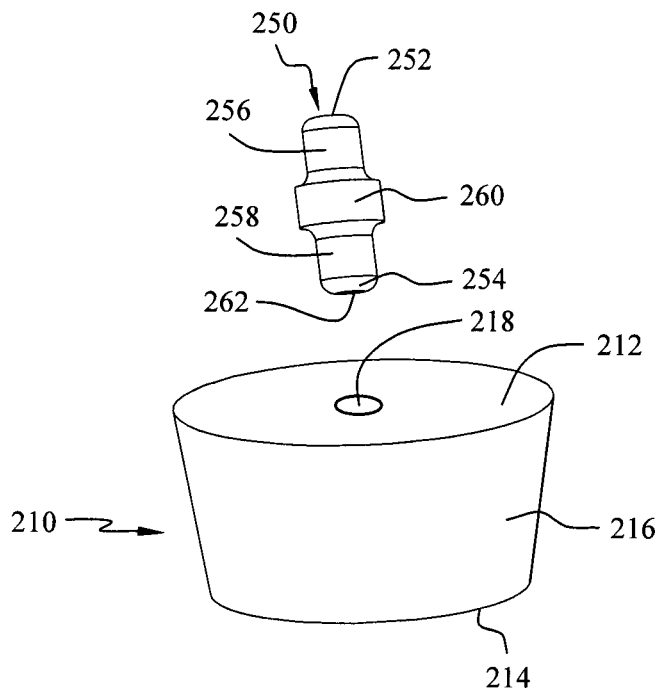
FIG. 15 is a perspective view of the stopper member of FIG. 14, in accordance with an aspect of the present invention.

Referring now to FIGS. 14 and 15, yet another embodiment of a stopper system 240 is shown. The stopper system 240 is a two piece system including a stopper member 210 and a fitting member 250. The stopper member 210 is of the type described above with reference to FIGS. 10 and 11, which will not be described again here for brevity sake. The fitting member 250 may include a first end 252 and a second end 254 opposite the first end 252. The fitting member 250 may also include a first receiving portion 256, a second receiving portion 258, and an intermediate portion 260 positioned between the first and second receiving portions 256, 258. The intermediate portion 260 may have, for example, a larger diameter than the first and second receiving portions 256, 258 and the receiving portions 256, 258 may have, for example, the same diameter. The first receiving portion 256 may be sized to be secured to a pressure delivery device, such as devices 190, 202, as described in greater detail below with reference to FIGS. 20 and 21. The second receiving portion 258 may be sized to be inserted into and secured to the opening 218 in the stopper member 210.

Figure 16:
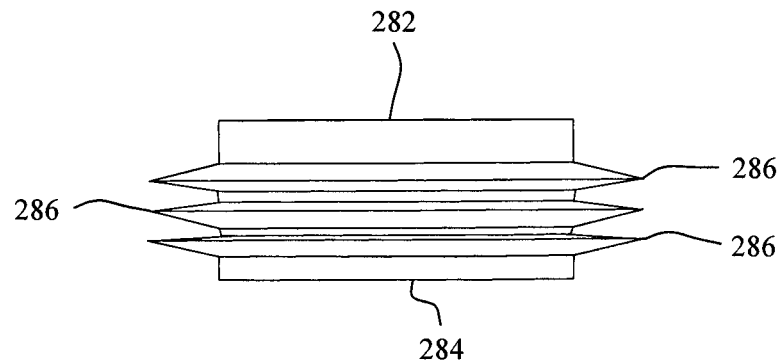
FIG. 16 is a side view of another stopper member, in accordance with an aspect of the present invention.
Figure 17:
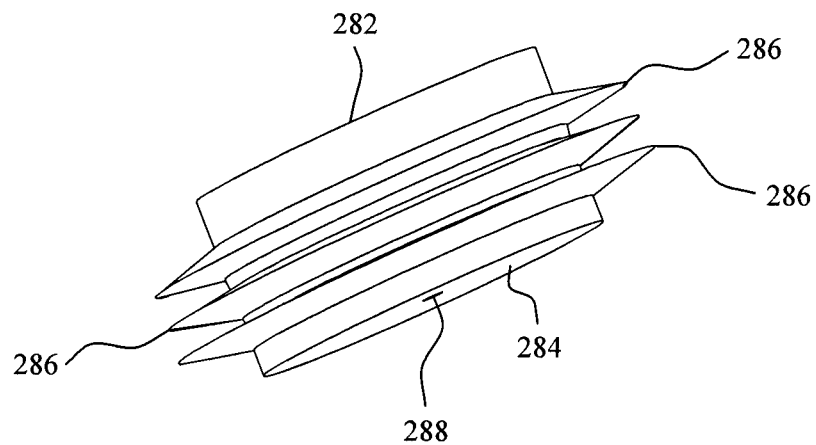
FIG. 17 is a perspective view of the stopper member of FIG. 16, in accordance with an aspect of the present invention.

FIGS. 16 and 17 show another stopper member 280. The stopper member 280 may include, for example, a first base portion at a first end 282, a second base portion at a second end 284, and a plurality of threads 286 extending between the first and second base portions on an exterior surface of the stopper member 280. The plurality of threads 286 may correspond to a plurality of threads (not shown) in the distal end of a container, chamber, or vial for securing the stopper member 280 to a container, chamber, or vial for administering a medication. The stopper member 280 may also include an opening 288 extending from the first end 282 to the second end 284 at, for example, a generally center point of the stopper member 280. The opening 288 may be sized to receive a pressure delivery device, such as devices 190, 202, as described in greater detail below with reference to FIGS. 20 and 21.

Figure 18:
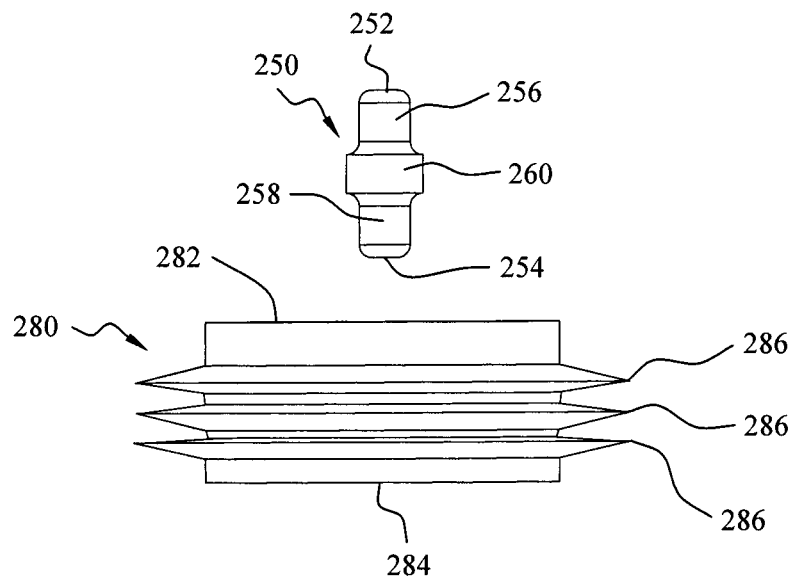
FIG. 18 is a side view of yet another stopper member, in accordance with an aspect of the present invention.
Figure 19:
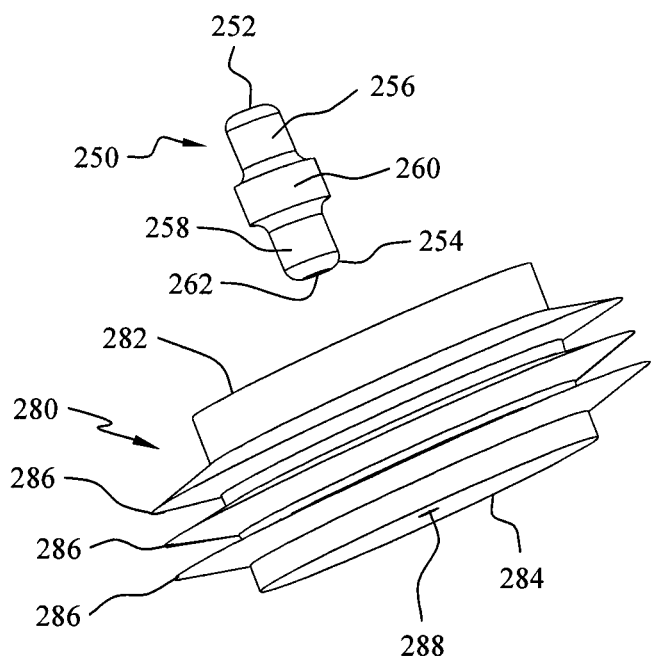
FIG. 19 is a perspective view of the stopper member of FIG. 18, in accordance with an aspect of the present invention.

Another stopper system 290 is shown in FIGS. 18 and 19. The stopper system 290 may include a stopper member 280 and a fitting member 250. The stopper member 280 may be of the type described above with reference to FIGS. 16 and 17 and the fitting member 250 may be of the type described above with reference to FIGS. 14 and 15. The stopper member 280 and fitting member 250 will not be described again here in detail for brevity sake. The first receiving portion 256 of the fitting member 250 may be sized to be secured to a pressure delivery device, such as devices 190, 202, as described in greater detail below with reference to FIGS. 20 and 21. The second receiving portion 258 of the fitting member 250 may be sized to be inserted into and secured to the opening 288 in the stopper member 280. The fitting member 250 may include, for example, a plurality of threads (not shown) positioned on the exterior surface of the second receiving portion 258. The plurality of threads on the second receiving portion 258 may correspond to a plurality of threads (not shown) on the interior surface of the opening 288 for securing the fitting member 250 to the stopper member 280. Alternative securement means, for example, adhesives, one piece molding, press-fit, and the like are also contemplated to secure the fitting member 250 to the stopper member 280.

Figure 20:
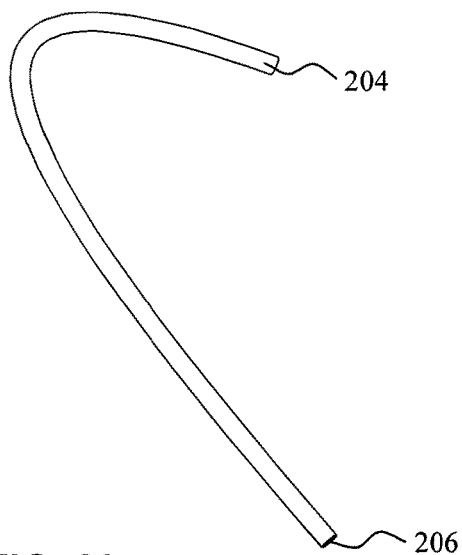
FIG. 20 is a perspective view of a pressure delivery device, in accordance with an aspect of the present invention.

FIG. 20 shows the pressure delivery device 202. As described above with reference to FIGS. 10 and 11, the pressure delivery device 202 may include a first end 204 and a second end 206. The pressure delivery device 202 may be, for example, a tube or other hollow elongated structure to allow for a pressurized media to pass from the first end 204 to the second end 206. The first end 204 may be sized to couple to a pressure delivery system (not shown) to deliver a pressurized fluid to a syringe container, chamber, or vial (not shown) for delivery of a medication to a patient. The second end 206 may be sized to be secured to a stopper member 210, 220, 240, 280, 290 either directly or using a separate or integral fitting member 230, 250.

Figure 21:
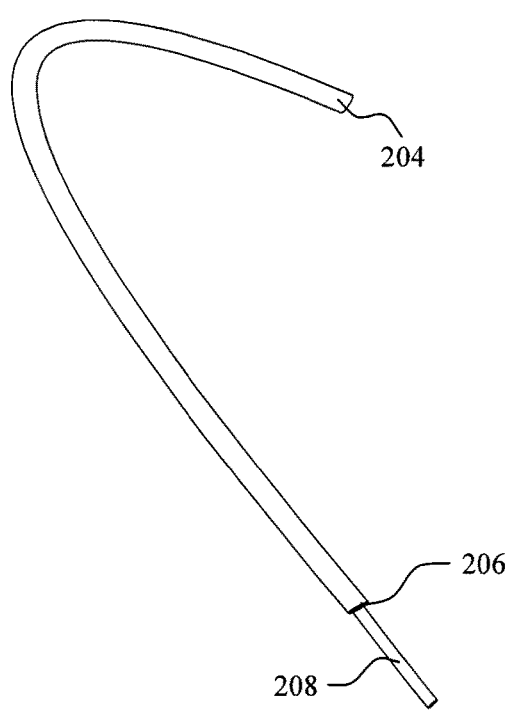
FIG. 21 is a perspective view of another pressure delivery device, in accordance with an aspect of the present invention.
Figure 22:
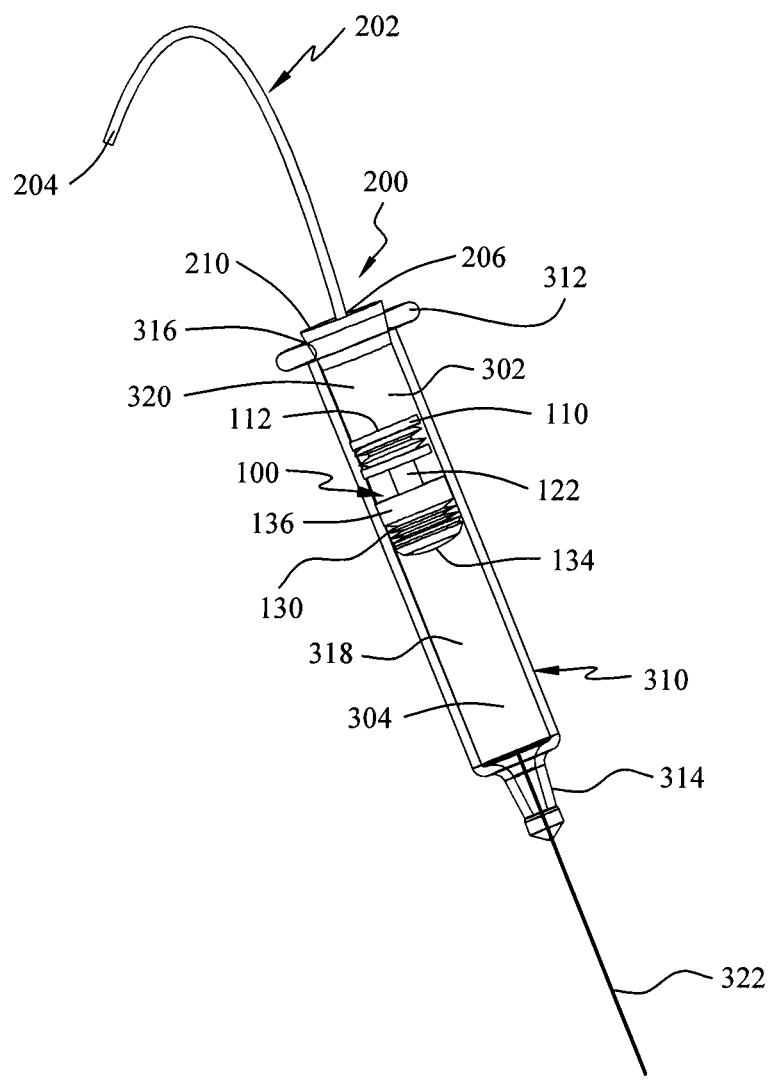
FIG. 22 is a side perspective view of a syringe system, in accordance with an aspect of the present invention.
Figure 23:
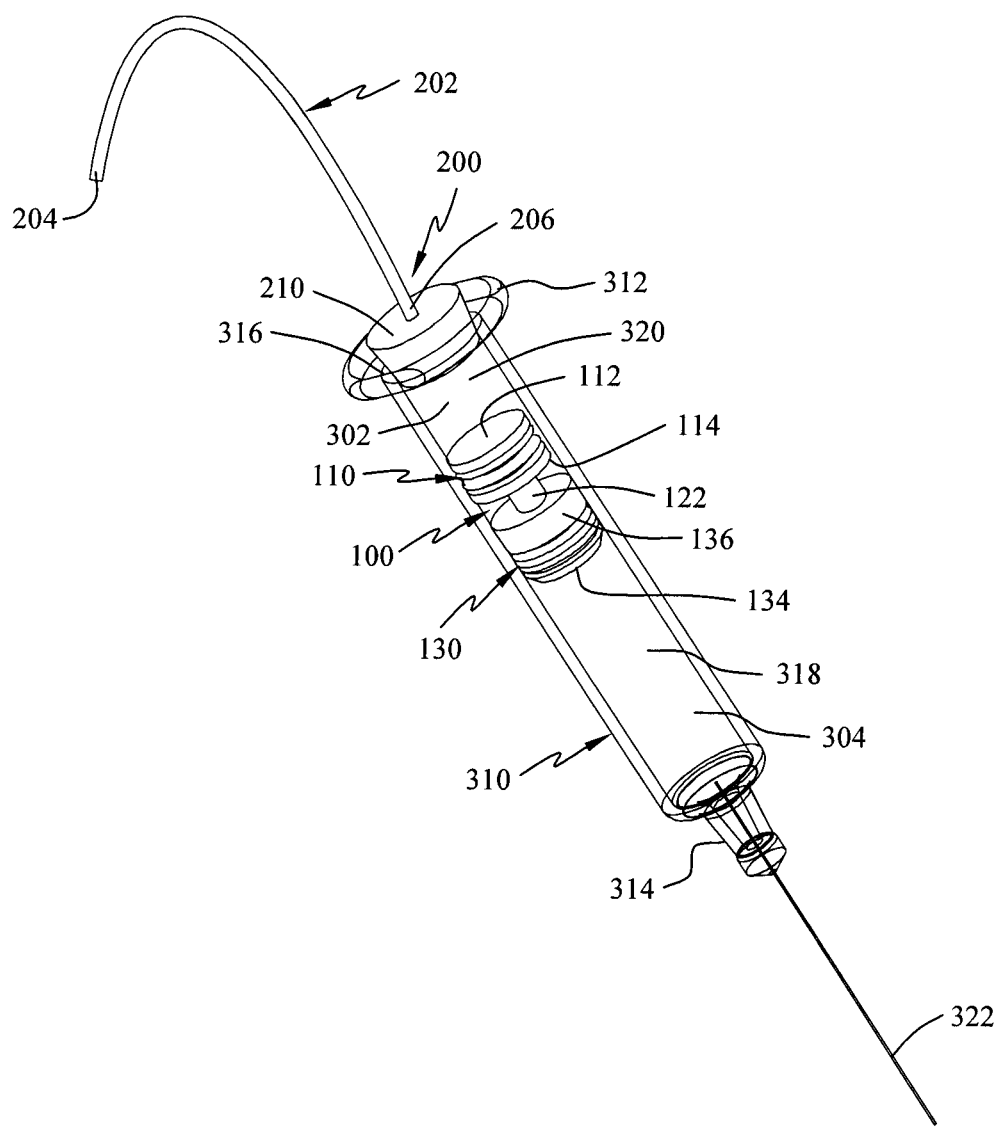
FIG. 23 is a top perspective view of the syringe system of FIG. 22, in accordance with an aspect of the present invention.

Referring now to FIG. 21, an alternative pressure delivery device 190 is shown. The pressure delivery device 190 may include a first end 204, a second end 206, and a staking needle 208. The pressure delivery device 190 may be, for example, a tube or other hollow structure to allow for fluid to pass from the first end 204 to the second end 206 and then through the staking needle 208 to the syringe container, chamber, or vial (not shown). The staking needle 208 may be secured to the second end 206. The staking needle 208 may be, for example, inserted directly into the stopper member 210, 280 without the need for the stopper member to include the opening 218, 288. Alternative pressure delivery devices 202, 190 are also contemplated for transferring a pressurized media from a pressure delivery system to a syringe container, chamber, or vial to move a piston seal system, such as systems 100, 150, or 170, to deliver a medication to a patient.

Referring now to FIGS. 22-25, an exemplary embodiment of an injection system 300 is shown. The injection system 300 may include a container 310, a fluid pathway 322, a stopper system 200, and a syringe piston seal system 100. The container 310 may include a first end for receiving the stopper system 200 and a second end for receiving the fluid pathway 322. The syringe piston seal system 100 may be sized to fit into an opening 316 in the container 310. The exterior surface of the piston seal system 100 is sized to engage the interior surface or walls of the container 310. The container 310 may be in, for example, a syringe, vial, or other container used for administering medication or fluids to a patient. The container 310 may be made of, for example, plastic, glass, metal, or any other material suitable for storing and delivering medication or fluids to a patient.

In the depicted embodiment of FIGS. 22-25, the first end of the container 310 may include, for example, a flange 312 surrounding the opening 316. The second end of the container 310 may include an attachment portion 314 for receiving a fluid pathway 322. The fluid pathway 322 may be, for example, a needle, cannula, or other device for delivering medication to a patient. The container 310 includes a cavity or chamber 318, 320 extending from the opening 316 to the attachment portion 314. The attachment portion 314 couples the chamber 318, 320 to the fluid pathway 322 allowing fluid to pass from the chamber 318, 320 to the fluid pathway 322. The container 310 may have, for example, any shape which is desirable for storing and delivering the medication or fluids to a patient and the syringe piston seal system 100 may have a shape to correspond to the shape of the opening 316 in the container 310.

The injection system 300 may be assembled by inserting a fluid pathway 322 into the container 310. Although not shown, it is preferred that the fluid pathway 322 be capped to ensure medication is not released from the fluid pathway 322 prior to the medication being administered. In addition, it is desirable to cap the fluid pathway 322 to prevent accidental sticks with the fluid pathway 322. Next, the chamber 318, 320 may be filled with the desired amount of medication 304 by known filling methods. Once the desired amount of medication 304 is contained within the chamber 318, 320, the syringe piston seal system 100 may be inserted into the opening 316. When the syringe piston seal system 100 is inserted into the container 310 the chamber 318, 320 is divided into a first chamber 318 at the second end of the container 310 and a second chamber 320 at the first end of the container 310. Alternatively, the chamber 318 may be filled by known methods with the desired amount of medication 304 after the syringe piston seal system 100 is inserted into the opening 316 in the container 310. The syringe piston seal system 100 may be made of, for example, any material that allows for sliding movement of the system 100 within the container 310 while maintaining separation between the pressurized fluid 302 and medication 304. The material of the syringe piston seal system 100 may be selected based on the medication 304 being injected and pressurized fluid 302 being used to ensure that no contamination of the sterilize medication 304 occurs. Although the syringe piston seal system 100 is shown, the syringe piston seal systems 150, 170, and other combinations thereof may also be used.

Once the medication 304 and syringe piston seal system 100 are within the container 310, then a stopper system 200 may be secured to the distal end of the container 310. The stopper system 200 may be inserted into the container 310, for example, so that the second end 214 of the stopper system 200 directly contacts the first end 112 of the piston seal member 110. The stopper system 200 may be secured by inserting the stopper member 210 into the opening 316 to close the chamber 320. Although the stopper system 200 is shown, other stopper systems may also be used including, for example, stopper members 220, 280, and combinations thereof. The stopper system 200 may also include a pressure delivery device 202 which may be coupled to a pressure delivery system at a first end 204 and to the stopper member 210 at a second end 206.

After the injection system 300 is assembled, the system 300 may be used for an injection. The injection system 300 may be used for an injection by turning on the connected pressure delivery device to start the flow of a pressurized media 302 through the pressure delivery device 202 and into the chamber 320. As the pressurized media 302 fills the chamber 320 at the distal end of the container 310, force is applied to the first end 112 of the piston seal member 110 by the pressurized media 302. In one embodiment, the injection system 300 may include, for example, at least one one-way vent to allow for the release of air or gas from the container 310 if the pressurized media 302 is a liquid. The piston seal member 110 and the piston head member 130 are each sized to prevent the pressurized media 302 from leaking into the medication 304, thus providing a barrier to isolate the pressurized media 302 from the medication 304. However, if fluid 302, 304 does leak, the space created around the coupling member 122 may trap the fluid 302, 304 from escaping and contaminating the medication 304. The flange members 116, 118 and grooves 120 of the seal member 110 and the flange members 138 and recesses 140 of the head member 130 may also act to assist with trapping any fluid 302, 304 that may leak and prevent the leaked pressurized fluid 302 from contaminating the medication 304.

Figure 24:
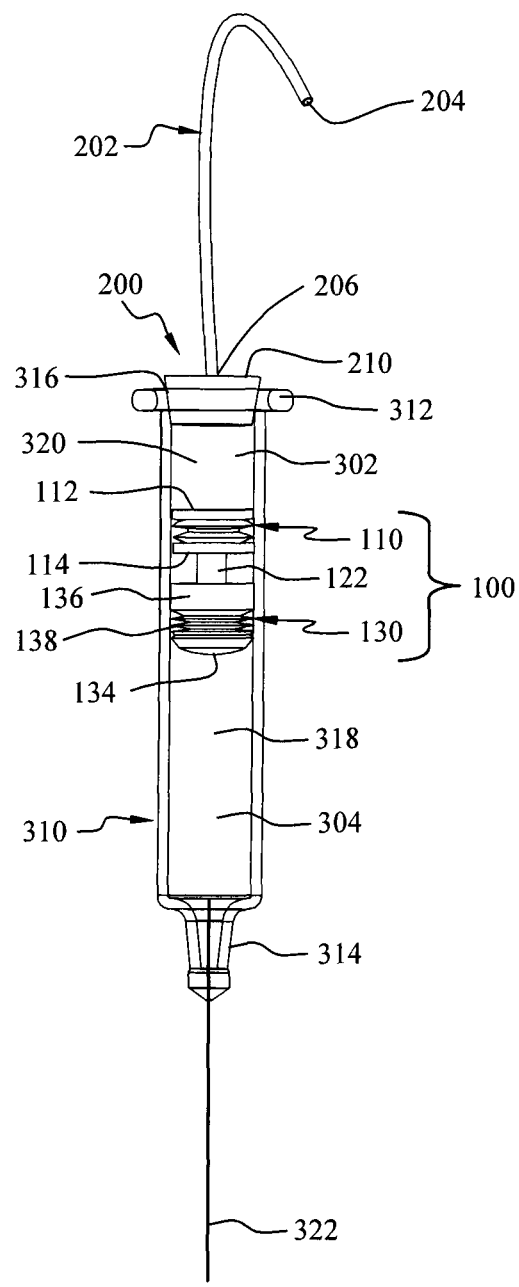
FIG. 24 is a side view of the syringe system of FIG. 22 with the piston seal system of FIG. 1 in a first position, in accordance with an aspect of the present invention.
Figure 25:
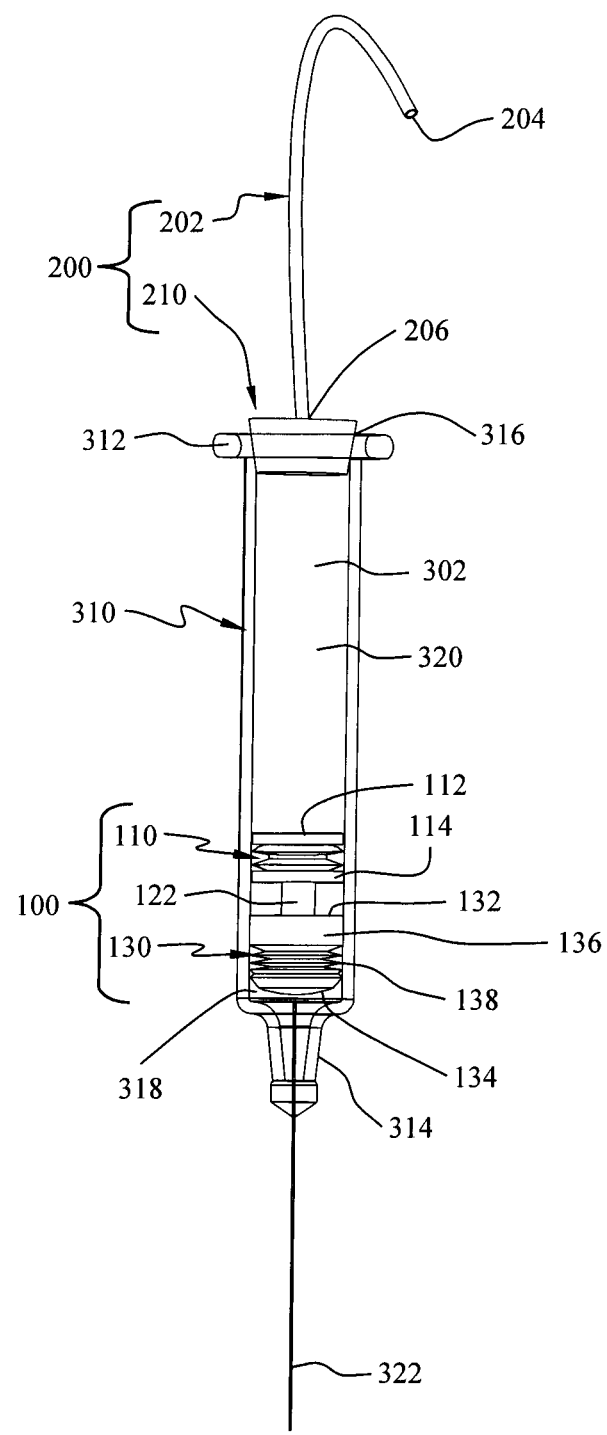
FIG. 25 is a side view of the syringe system of FIG. 22 with the piston seal system of FIG. 1 in a second position, in accordance with an aspect of the present invention.

Once the force being applied to the piston seal member 110 is sufficient to generate a resultant force great enough to overcome the inherent frictional wall forces on the corresponding piston seal system 100, the piston seal system 100 begins to move toward the attachment portion 314 at the proximal end of the container 310. As the piston seal system 100 moves, the fluid resistance in the fluid pathway 322 is overcome and the medication 304 is forced out of the fluid pathway 322 for delivery to the patient. Referring now to FIGS. 24 and 25, FIG. 24 illustrates the position of the piston seal system 100 when the pressurized media 302 begins to be pumped into the chamber 318. FIG. 25 shows the position of the piston seal system 100 after all of the medication 304 is delivered to the patient.

Figure 26:
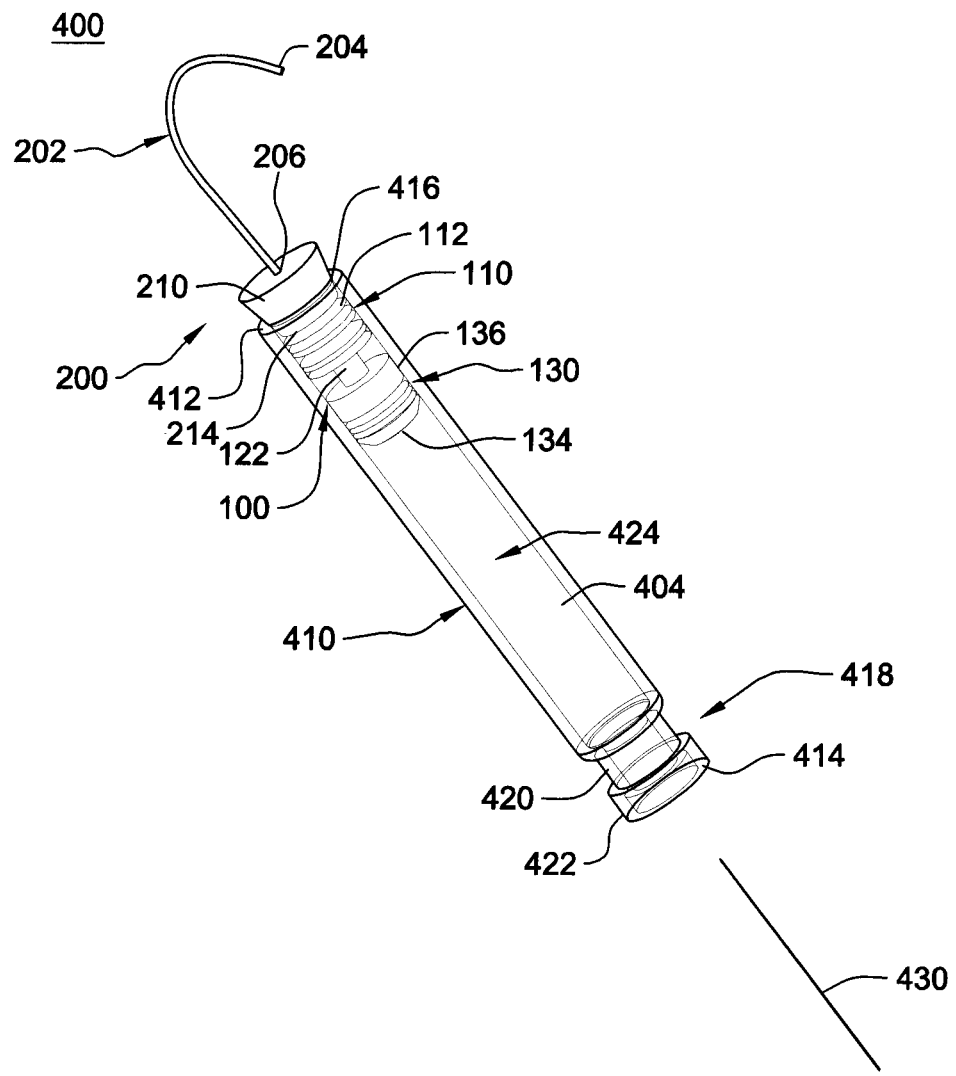
FIG. 26 is a partially exploded, side perspective view of a cartridge system with the piston seal system of FIG. 1 in a first position, in accordance with an aspect of the present invention.
Figure 27:
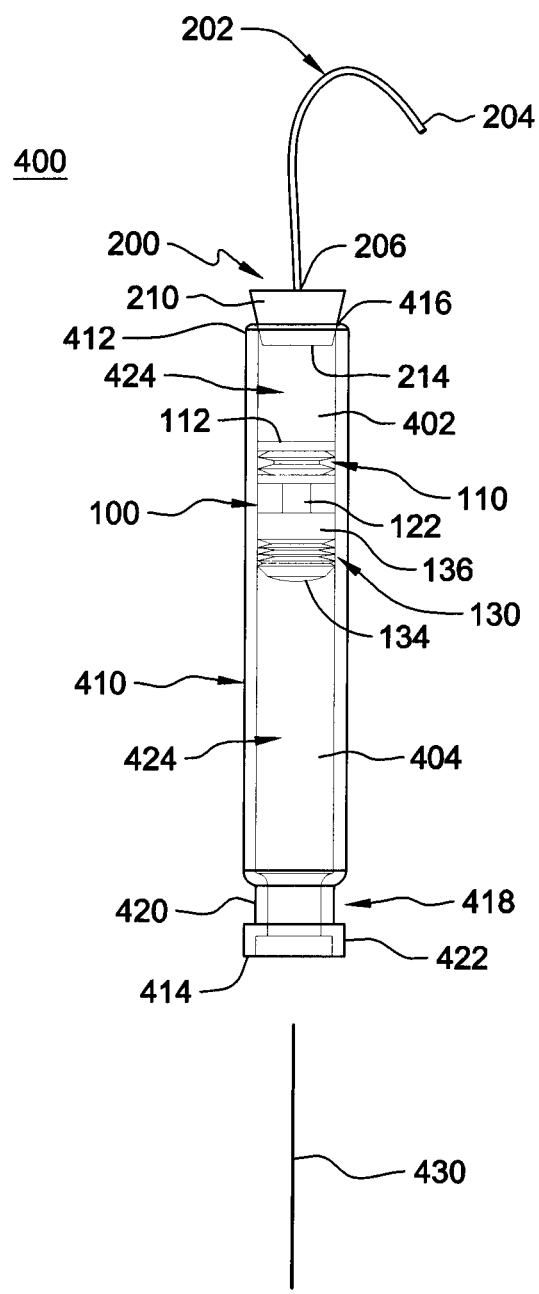
FIG. 27 is a side view of a cartridge system of FIG. 26, in accordance with an aspect of the present invention.
Figure 28:
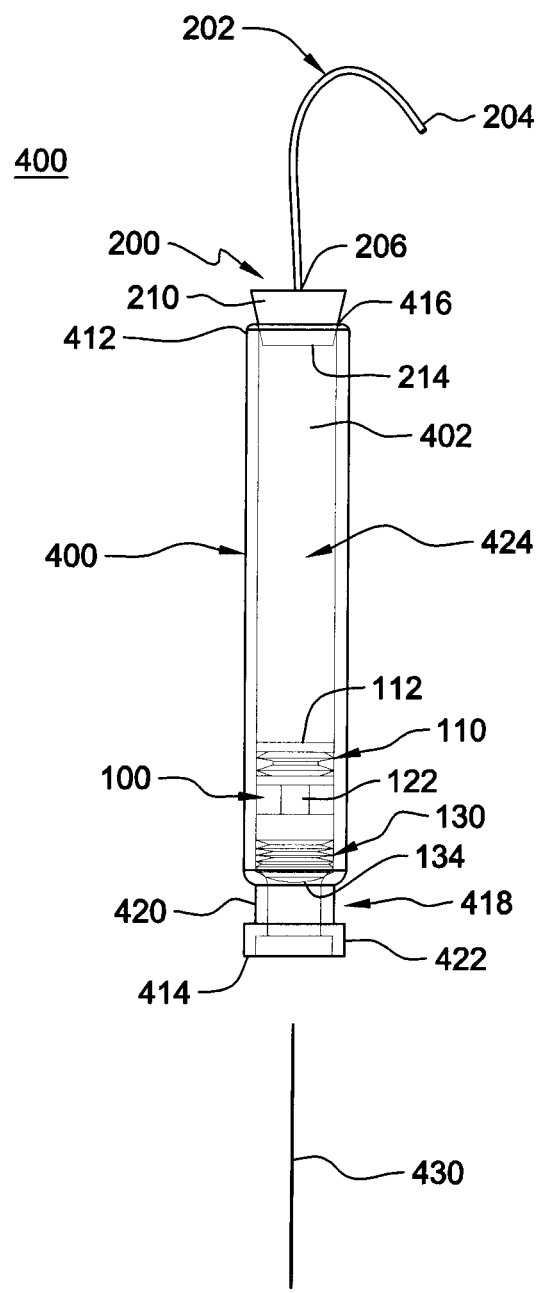
FIG. 28 is a side view of a cartridge system of FIG. 26 with the piston seal system of FIG. 1 in a second position, in accordance with an aspect of the present invention.

Referring now to FIGS. 26-28, an exemplary embodiment of an injection system 400 is shown. The injection system 400 may include a container 410, a fluid pathway 430, a stopper system 200, and a piston seal system 100. The container 410 may include a first end for receiving the stopper system 200 and a second end for receiving the fluid pathway 430. The piston seal system 100 may be sized to fit into an opening 416 in the container 410. The exterior surface of the piston seal system 100 is sized to engage the interior surface or walls of the container 410. The container 410 may be in, for example, a cartridge, vial, syringe, or other container used for administering medication or fluids to a patient. The container 410 may be made of, for example, plastic, glass, metal, or any other material suitable for storing and delivering medication or fluids to a patient.

In the depicted embodiment of FIGS. 26-28, the container 410 may include, for example, a first end 412 and a second end 414. The second end 414 may include an attachment portion 418 for receiving a fluid pathway 430. The attachment portion 418 may include, for example, a neck portion 420 and a flange portion 422. The neck portion 420 may have, for example, a smaller diameter than the container 410 and the flange portion 422. The fluid pathway 430 may be, for example, a needle, cannula, or other device for delivering medication to a patient. The container 410 includes a chamber or cavity 424 extending from the opening 416 to the attachment portion 418. The attachment portion 418 couples the chamber 424 to the fluid pathway 430 allowing fluid to pass from the chamber 424 to the fluid pathway 430. The container 410 may have, for example, any shape which is desirable for storing and delivering the medication or fluids to a patient and the piston seal system 100 may have a shape to correspond to the shape of the opening 416 in the container 410.

The injection system 400 may be assembled by inserting a fluid pathway 430 into the container 410. Although not shown, it is preferred that the fluid pathway 430 be capped to ensure medication is not released from the fluid pathway 430 prior to the medication being administered and to prevent accidental contacts with the fluid pathway 430. Next, the chamber 424 may be filled with the desired amount of medication by known filling methods. Once the desired amount of medication is transported into the chamber 424, the piston seal system 100 may be inserted into the opening 416. When the piston seal system 100 is inserted into the chamber 424 of the container 410 it is positioned at the first end of the container 410, as shown in FIG. 26. Alternatively, the chamber 424 may be filled by known methods with the desired amount of medication after the piston seal system 100 is inserted into the opening 416 in the container 410. The piston seal system 100 may be made of, for example, any material that allows for sliding movement of the system 100 within the container 410 while maintaining separation between the medication and the pressurized fluid injected into the container 410 by the pressure delivery device 202. The material of the piston seal system 100 may be selected based on the medication being injected and pressurized fluid being used to ensure that no contamination of the sterilize medication occurs. Although the piston seal system 100 is shown, the piston seal systems 150, 170, and other combinations thereof may also be used.

Once the medication and piston seal system 100 are inside the container 410, then a stopper system 200 may be secured to the distal end of the container 410. The stopper system 200 may be inserted into the container 410, for example, so that the second end 214 of the stopper system 200 directly contacts the first end 112 of the piston seal member 110, as shown in FIG. 26. The stopper system 200 may be secured by inserting the stopper member 210 into the opening 416 to close the chamber 424. Although the stopper system 200 is shown, other stopper systems may also be used including, for example, stopper members 220, 280, and combinations thereof. The stopper system 200 may also include a pressure delivery device 202 which may be coupled to a pressure delivery system at a first end 204 and to the stopper member 210 at a second end 206.

After the injection system 400 is assembled, the system 400 may be used for an injection. The injection system 400 may be used for an injection by turning on the connected pressure delivery device to start the flow of a pressurized media 402 through the pressure delivery device 202 and into the chamber 424. As the pressurized media 402 fills the chamber 424 at the distal end of the container 410, force is applied to the first end 112 of the piston seal member 110 by the pressurized media 402. In one embodiment, the injection system 400 may include, for example, at least one one-way vent to allow for the release of air or gas from the container 410 if the pressurized media 402 is a liquid. The piston seal member 110 and the piston head member 130 are each sized to prevent the pressurized media 402 from leaking into the medication 404, thus providing a barrier to isolate the pressurized media 402 from the medication 404. However, if fluid 402, 404 does leak, the space created around the coupling member 122 may trap the fluid 402, 404 from escaping and contaminating the medication 404. The flange members 116, 118 and grooves 120 of the seal member 110 and the flange members 138 and recesses 140 of the head member 130 may also act to assist with trapping any fluid 402, 404 that may leak and prevent the leaked pressurized fluid 402 from contaminating the medication 404.

Once the force being applied to the piston seal member 110 is sufficient to generate a resultant force great enough to overcome the inherent frictional wall forces on the corresponding piston seal system 100, the piston seal system 100 begins to move toward the second or proximal end 414 of the container 410, as shown in FIG. 27. As the piston seal system 100 moves, the fluid resistance in the fluid pathway 430 is overcome and the medication 404 is forced out of the fluid pathway 430 for delivery to the patient. The position of the piston seal system 100 after all of the medication 404 is delivered to the patient is shown in FIG. 28.

As may be recognized by those of ordinary skill in the art based on the teachings herein, numerous changes and modifications may be made to the above-described and other embodiments of the present invention without departing from the scope of the invention. For example, injection systems may include more or fewer components or features than the embodiments as described and illustrated herein. For example, the components and features of FIGS. 1-5, FIGS. 6-7, and FIGS. 8-9 may all be used interchangeably and in alternative combinations as would be modified or altered by one of skill in the art. In addition, the components and features of FIGS. 10-11, FIGS. 12-13, FIGS. 14-15, FIGS. 16-17, and FIGS. 18-19 may all be used interchangeably and in alternative combinations as would be modified or altered by one of skill in the art. Accordingly, this detailed description of the currently-preferred embodiments is to be taken as illustrative, as opposed to limiting of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

In some embodiments, "a piston head member" may be referred to as "a piston," "pressurized fluid" may be referred to as a "first fluid," "medication" may be referred to as a "second fluid," and "flanges" may be referred to as "circumferential rings."

Having thus described the preferred embodiments, the invention is now claimed to be:

1. An injection device, comprising:
   a container having a first end and a second end;
   a piston configured to move toward the second end of the container;
   a seal disposed between the first end of the container and the piston, the seal being spaced apart from and coupled to the piston such that movement of the seal and the piston occur simultaneously, wherein an outer surface of the piston and an outer surface of the seal are configured to engage an interior surface of the container; and
   a pressure delivery device configured to convey a first fluid, from exterior of the container, into the container and into contact with the seal to urge initial movement of the seal and the piston from a resting position toward the second end of the container;
   wherein a second fluid is configured to be disposed in the container and in direct contact with the piston, wherein movement of the seal and the piston toward the second end of the container urges the second fluid out of the container, and further including a stopper configured to seal the first end of the container.

2. The injection device of claim 1, further including a needle coupled to the second end of the container.

3. The injection device of claim 1, further including a stopper configured to seal the first end of the container, wherein the piston is configured to move relative to the stopper.

4. The injection device of claim 3, wherein the pressure delivery device is configured to convey the first fluid through the stopper into the container.

5. The injection device of claim 1, wherein the first fluid is pressurized before delivery into the container.

6. The injection device of claim 1, wherein the piston includes a circumferential ring configured to seal against an inner surface of the container.

7. The injection device of claim 1, wherein the seal is coupled to the piston by a shaft.

8. The injection device of claim 7, wherein a diameter of the shaft is less than the outer diameter of the piston, and also is less than the outer diameter of the seal.

9. The injection device of claim 8, wherein a space between the seal and the piston is configured to contain any first fluid that leaks distally of the seal.

10. The injection device of claim 7, wherein the shaft is configured to prevent angular shift or tilting of the seal when the pressure delivery device conveys the first fluid into the container.

11. The injection device of claim 1, wherein the seal includes a circumferential ring configured to seal against an inner surface of the container.

12. The injection device of claim 1, wherein at least a portion of the stopper is disposed exterior of the container.

13. The injection device of claim 1, wherein at least a portion of the stopper is disposed within the container.

14. The injection device of claim 1, wherein the stopper is secured to the first end of the container.

15. An injection device, comprising:
a container having a first end and a second end;
a piston configured to move toward the second end of the container;
a seal disposed between the first end of the container and the piston, the seal being longitudinally spaced apart from the piston, wherein an outer surface of the piston and an outer surface of the seal are configured to engage an interior surface of the container;
a second fluid disposed between the piston and the second end of the container, wherein the piston directly contacts the second fluid; and
a pressure delivery device configured to convey a pressurized first fluid from exterior of the container, into the container and into contact with the seal to urge the seal and the piston toward the second end of the container to advance the second fluid out of the second end of the container, wherein a space between the piston and the seal is configured to trap any second fluid that leaks proximally past the piston, and trap any pressurized first fluid that leaks distally past the seal, wherein the first fluid is a gas that drives initial movement of the seal.

16. The injection device of claim 15, wherein the seal and the piston each includes a plurality of longitudinally spaced apart circumferential rings that are configured to seal against an inner surface of the container.

17. An injection device, comprising:
a container having a first end and a second end;
a piston configured to move toward the second end of the container;
a seal disposed between the first end of the container and the piston, the seal being spaced apart from and coupled to the piston such that movement of the seal and the piston occur simultaneously, wherein an outer surface of the piston and an outer surface of the seal are configured to engage an interior surface of the container;
a pressure delivery device configured to convey a first fluid, from exterior of the container, into the container and into contact with the seal to urge initial movement of the seal and the piston from a resting position toward the second end of the container; and
a stopper configured to seal the first end of the container, wherein the piston is configured to move relative to the stopper;
wherein a second fluid is configured to be disposed in the container between the piston and the second end of the container such that:
the piston is configured to directly contact the second fluid; and
movement of the seal and the piston toward the second end of the container is configured to urge the second fluid out of a distalmost portion of the container.

18. The injection device of claim 17, further including a needle coupled to the second end of the container.

19. The injection device of claim 17, wherein the pressure delivery device is configured to convey the first fluid through the stopper into the container.

20. The injection device of claim 17, wherein the first fluid is pressurized before delivery into the container.

21. The injection device of claim 17, wherein the first fluid is a gas.

* * * * *